United States Patent
Seet et al.

(10) Patent No.: US 11,680,244 B2
(45) Date of Patent: Jun. 20, 2023

(54) METHOD FOR GENERATING HUMAN DENDRITIC CELLS FOR IMMUNOTHERAPY

(71) Applicant: THE REGENTS OF THE UNIVERSITY OF CALIFORNIA, Oakland, CA (US)

(72) Inventors: Christopher S. Seet, Santa Monica, CA (US); Gay Miriam Crooks, Sherman Oaks, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 179 days.

(21) Appl. No.: 15/575,073

(22) PCT Filed: May 19, 2016

(86) PCT No.: PCT/US2016/033339
§ 371 (c)(1),
(2) Date: Nov. 17, 2017

(87) PCT Pub. No.: WO2016/187459
PCT Pub. Date: Nov. 24, 2016

(65) Prior Publication Data
US 2018/0155688 A1  Jun. 7, 2018

Related U.S. Application Data

(60) Provisional application No. 62/164,368, filed on May 20, 2015.

(51) Int. Cl.
C12N 5/10 (2006.01)
C12N 5/0784 (2010.01)
A61K 39/00 (2006.01)

(52) U.S. Cl.
CPC ........ *C12N 5/0639* (2013.01); *A61K 39/0011* (2013.01); *A61K 39/00115* (2018.08); *A61K 39/00117* (2018.08); *A61K 39/001104* (2018.08); *A61K 39/001106* (2018.08); *A61K 39/001108* (2018.08); *A61K 39/001109* (2018.08); *A61K 39/001122* (2018.08); *A61K 39/001149* (2018.08); *A61K 39/001151* (2018.08); *A61K 39/001153* (2018.08); *A61K 39/001156* (2018.08); *A61K 39/001157* (2018.08); *A61K 39/001164* (2018.08); *A61K 39/001168* (2018.08); *A61K 39/001171* (2018.08); *A61K 39/001172* (2018.08); *A61K 39/001182* (2018.08); *A61K 39/001186* (2018.08); *A61K 39/001188* (2018.08); *A61K 39/001191* (2018.08); *A61K 39/001192* (2018.08); *A61K 39/001193* (2018.08); *A61K 39/001194* (2018.08); *A61K 39/001195* (2018.08); *A61K 39/001197* (2018.08); *A61K 2039/5154* (2013.01); *C12N 2500/30* (2013.01); *C12N 2501/125* (2013.01); *C12N 2501/145* (2013.01); *C12N 2501/22* (2013.01); *C12N 2501/2303* (2013.01); *C12N 2501/26* (2013.01); *C12N 2501/42* (2013.01); *C12N 2501/998* (2013.01); *C12N 2502/1121* (2013.01); *C12N 2502/1171* (2013.01); *C12N 2502/1352* (2013.01)

(58) Field of Classification Search
None
See application file for complete search history.

(56) References Cited

U.S. PATENT DOCUMENTS

| | | |
|---|---|---|
| 5,389,640 A | 2/1995 | Gerster et al. |
| 6,110,929 A | 8/2000 | Gerster et al. |
| 6,331,539 B1 | 12/2001 | Crooks et al. |
| 6,451,810 B1 | 9/2002 | Coleman et al. |
| 7,795,404 B1 | 9/2010 | Lin et al. |
| 8,021,867 B2 | 9/2011 | Smith et al. |
| 8,377,886 B2 | 2/2013 | Susztak et al. |
| 10,350,243 B2 | 7/2019 | Zakrzewski et al. |
| 2003/0109042 A1 | 6/2003 | Wu et al. |
| 2004/0171086 A1 | 9/2004 | Fink et al. |
| 2004/0171148 A1 | 9/2004 | Schmitt et al. |
| 2005/0123522 A1 | 6/2005 | Punnonen et al. |
| 2006/0073591 A1 | 4/2006 | Abitorabi et al. |
| 2009/0253622 A1 | 10/2009 | Van Noort et al. |
| 2010/0279403 A1 | 11/2010 | Rajesh et al. |
| 2011/0052554 A1 | 3/2011 | Zakrzewski et al. |

(Continued)

FOREIGN PATENT DOCUMENTS

| | | |
|---|---|---|
| EP | 2906684 | 7/2020 |
| JP | 2012-509659 | 4/2012 |
| WO | WO 98/30679 | 7/1998 |

(Continued)

OTHER PUBLICATIONS

Sotiropoulou et al. (2006) Stem Cell 24:462-471.*
Zeng et al. (2014) Stem Cell Translational Medicine 3: 69-80.*
Zuniga-Pflucker (2004) Nature Review Immunology 4:67-72.*
Balan, et al., "Human XCR1+ Dendritic Cells Derived in Vitro from CD34+ Progenitors Closely Resemble Blood Dendritic Cells, Including Their Adjuvant Responsiveness, Contrary to Monocyte-Derived Dendritic Cells," *The Journal of Immunology*, 193(4); 1622-1635, 2014.

(Continued)

*Primary Examiner* — Michael D Pak
(74) *Attorney, Agent, or Firm* — Norton Rose Fulbright US LLP

(57) ABSTRACT

In various embodiments methods of producing a cell population enriched for CLEC9A+ dendritic cells are provided where the methods involve culturing stem cells and/or progenitor cells in a cell culture comprising culture medium, a notch ligand, stem cell factor (SCF), FLT3 ligand (FLT3L); thrombopoietin (TPO); and IL-3 and/or GMCSF.

11 Claims, 4 Drawing Sheets

(56) References Cited

U.S. PATENT DOCUMENTS

2011/0236363 A1  9/2011  Chang et al.
2015/0299656 A1  10/2015  Gattinoni et al.

FOREIGN PATENT DOCUMENTS

| WO | WO 2000/076518 | 12/2000 |
|---|---|---|
| WO | WO 2007/027226 | 3/2007 |
| WO | WO 2011/101468 | 8/2011 |
| WO | WO 2011/131944 | 10/2011 |
| WO | WO 2012/027017 | 3/2012 |
| WO | WO 2014/138315 | 9/2014 |

OTHER PUBLICATIONS

European Search Report Issued in European Application No. 16797322. 1, dated Sep. 28, 2018.
Alexopoulou, et al., "Recognition of Double-Stranded RNA and Activation of NF-κB by Toll-Like Receptor 3," Nature, 413(6857), pp. 732-738. (2001).
Baurain, et al., "High Frequency of Autologous Anti-Melanoma CTL Directed Against an Antigen Generated by a Point Mutation in a New Helicase Gene," Journal of Immunology, 164 pp. 6057-6066. (2000).
Brandie, et al., "A Mutated HLA-A2 Molecule Recognized by Autologous Cytotoxic T Lymphocytes on a Human Renal Cell Carcinoma," Journal of Experimental Medicine, 183, pp. 2501-2508. (1996).
Caminschi, et al., "The Dendritic Cell Subtype-Restricted C-type Lectin Clec9A is a Target for Vaccine Enhancement," Blood, 112(8), pp. 3264-3273. (2008).
Cheever, et al., "The Prioritization of Cancer Antigens: A National Cancer Institute Pilot Project for the Acceleration of Translational Research," Clinical Cancer Research, 15(17), pp. 5323-5337. (2009).
Cheng, et al., "Notch Signaling in Differentiation and Function of Dendritic Cells," Immunologic Research, 41(1), pp. 1-14. (2008). NIH Public Access Author Manuscript Retrieved from https://www.ncbi.nlm.nih.gov/pmc/articles/PMC2709100/pdf/nihms113342.pdf.
Chiari, et al., "Two Antigens Recognized by Autologous Cytolytic T Lymphocytes on a Melanoma Result from a Single Point Mutation in an Essential Housekeeping Gene," Cancer Research, 59, pp. 5785-5792. (1999).
Corbiere, et al., "Antigen Spreading Contributes to MAGE Vaccination-Induced Regression of Melanoma Metastases," Cancer Research, 71, pp. 1253-1262. (2011).
Coulie, et al., "A Mutated Intron Sequence Codes for an Antigenic Peptide Recognized by Cytolytic T Lymphocytes on a Human Melanoma," Proceedings of the National Academy of Sciences of the United States of America, 92(17), pp. 7976-7980. (1995).
Echchakir, et al., "A Point Mutation in the α-Actinin-4 Gene Generates an Antigenic Peptide Recognized by Autologous Cytolytic T Lymphocytes on a Human Lunch Carcinoma," Cancer Research, 61, pp. 4078-4083. (2001).
Gaudin, et al., "A hsp70-2 Mutation Recognized by CTL on a Human Renal Cell Carcinoma," Journal of Immunology, 162(3), pp. 1730-1738. (1999).
Hogan, et al., "The Peptide Recognized by HLA-A68.2-Restricted, Squamous Cell Carcinoma of the Lung-Specific Cytotoxic T Lymphocytes is Derived From a Mutated Elongation Factor 2 Gene[1]," Cancer Research, 58, pp. 5144-5150. (1998).
Huang, et al., "T Cells Associated with Tumor Regression Recognize Frameshifted Products of the CDKN2A Tumor Suppressor Gene Locus and a Mutated HLA Class I Gene Product," Journal of Immunology, 172(10), pp. 6057-6064. (2005).
International Preliminary Report on Patentability Issued in Corresponding PCT Application No. PCT/US2016/033339, dated Nov. 21, 2017.
International Search Report and Written Opinion Issued in Corresponding PCT Application. No. PCT/US2016/033339, dated Sep. 6, 2016.
Karanikas, et al., "High Frequency of Cytolytic T Lymphocytes Directed Against a Tumor-Specific Mutated Antigen Detectable with HLA Tetramers in the Blood of a Lunch Carcinoma Patient with Long Survival," Cancer Research, 61, pp. 3718-3724. (2001).
Kawakami, et al., "Isolation of a New Melanoma Antigen, MART-2, Containing a Mutated Epitope Recognized by Autologous Tumor-Infiltrating T Lymphocytes," Journal of Immunology, 166, pp. 2871-2877. (2001).
Kokatla, et al., "Structure-Based Design of Novel Human Toll-Like Receptor 8 Antagonists," ChemMedChem, 9(4), pp. 719-723. (2014). NIH Public Access Author Manuscript Retrieved from https://www.ncbi.nlm.nih.gov/pmc/articles/PMC4105021/pdf/nihms-577383.pdf.
Lamott-Mohs, et al., "Induction of T-Cell Development from Human Cord Blood Hematopoietic Stem Cells by Delta-like 1 In Vitro," Blood, 105(4), pp. 1431-1439. (2005).
Lee et al., "Restricted Dendritic Cell and Monocyte Progenitors in Human Cord Blood and Bone Marrow," Journal of Experimental Medicine, 212(3), pp. 385-399. (2015).
Lei, et al., "Aire-Dependent Production of XCL1 Mediates Medullary Accumulation of Thymic Dendritic Cells and Contributes to Regulatory T Cell Development," Journal of Experimental Medicine, 208(2), pp. 383-394. (2011).
Lennerz, et al., "The Response of Autlogous T Cells to a Human Melanoma is Dominated by Mutated Neoantigens," Proceedings of the National Academy of Sciences of the United States of America, 102(44), pp. 16013-16018. (2005).
Lu & Robbins, "Cancer Immunotherapy Targeting Neoantigens," Seminars Immunol., 28(1), pp. 22-27. (2016). Retrieved from HHS Public Access, Author Manuscript Retrieved from https://www.ncbi.nlm.nih.gov/pmc/articles/PMC4862880/pdf/nihms-737023.pdf.
Lu, et al., "Mutated PPP1R3B is Recognized by T Cells Used to Treat a Melanoma Patient Who Experienced a Durable Complete Tumor Regression," Journal of Immunology. 190, pp. 6034-6042. (2013).
Mandruzzato, et al., "A CASP-8 Mutation Recognized by Cytolytic T Lymphocytes on a Human head and Neck Carcinoma," Journal of Experimental Medicine, 186, pp. 785-793. (1997).
Novellino., et al., "Identification of a Mutated Receptor-Like Protein Tyrosine Phosphatase K as a Novel, Class II HLA-Restricted Melanoma Antigen," Journal of Immunology, 170(12), pp. 6363-6370. (2003).
Ohishi, et al., "The Notch Ligand, Delta-1, Inhibits the Differentiation of Monocytes in Macrophages but Permits Their Differentiation into Dendritic Cells," Blood, 98(5), pp. 1402-1407. (2001).
Olivier, et al., "The Notch Ligand Delta-1 is a Hematopoietic Development Cofactor for Plasmacytoid Dendritic Cells," Blood, 107(7), pp. 2694-2701. (2006).
Palucka & Banchereau, "Cancer Immunotherapy Via Dendritic Cells," Nature Reviews Cancer, 12(4), pp. 265-277. (2012). NIH Public Access Author Manuscript Retrieved from https://www.ncbi.nlm.nih.gov/pmc/articles/PMC3433802/pdf/nihms397786.pdf.
Pieper, et al., "Biochemical Identification of a Mutated Human Melanoma Antigen Recognized by CD4+ T Cells," Journal of Experimental Medicine, 189(5), pp. 757-765. (1999).
Poulin, et al., "Characterization of Human DNGR-1 + BDCA+ Leukocytes as Putative Equivalents of Mouse CD8α+ Dendritic Cells," Journal of Experimental Medicine, 207(6), pp. 1261-1271. (2010).
Proietto, et al., "The Equivalents in Human Blood and Spleen Dendritic Cell Subtypes can be Generated In Vitro from Human Stem Cells in the Presence of FMS-Like Tyrosine Kinase 3 Ligand and Thrombopoietin," Cellular & Molecular Immunology, 9, pp. 446-454. (2012).
Robbins, et al., "A Mutated Beta-Catenin Gene Encodes a Melanoma-Specific Antigen Recognized by Tumor Infiltrating Lymphocytes," Journal of Experimental Medicine, 183(3), pp. 1185-1192. (1996).
Sensi, et al., "Immunogenicity Without Immunoselection," A Mutant but Functional Antioxidant Enzyme Retained in a Human Metastatic Melanoma and Targeted by CD8+ T Cells with a Memory Phenotype, Cancer Research, 65(2), pp. 632-640. (2005).
Takenoyama, et al., "A Point Mutation in the NFYC Gene Generates an Antigenic Peptide Recognized by Autlogous Cytolytic T Lym-

(56) References Cited

OTHER PUBLICATIONS phocytes on a Human Squamous Cell Lung Carcinoma," *International Journal of Cancer*, 118, pp. 1992-1997. (2006).
Thordadottir, et al., "The Aryl Hydrocarbon Receptor Antagonist StemReginin 1 Promotes Human Plasmacytoid and Myeloid Dendritic Cell Development from CD34 Hematopoietic Progenitor Cells," *Stem Cells and Development*, 23(9), pp. 955-967. (2014).
Tullett, et al., "Harnessing Human Cross-Presenting CLEC9A+ XRC1+ Dendritic Cells for Immunotherapy," *Frontiers in Immunology*, 5(239), pp. 1-4. (2014).
Van Der Aa, et al., "BDCA3+CLEC9A+ Human Dendritic Cell Function and Development," *El Sevier, Seminars in Cell & Developmental Biology*, 41, pp. 39-48.(2014).
Vigneron, et al., "Identification of a New Peptide Recognized by Autologous Cytolytic T Lymphocytes on a Human Melanoma," *Cancer Immunity*, 2, pp. 9. (2002). Retrieved from https://pdfs.semanticscholar.org/b9fc/57a60dfc33ed4d5103e25277b204dcc9e3e0.pdf.
Wang, et al., "Cloning Genes Encoding MHC Class Il-Restricted Antigens: Mutated CDC27 as a Tumor Antigen," *Science*, 284, pp. 1351-1354. (1999).
Wang, et al., "Identification of a Mutated Fibronectin as a Tumor Antigen Recognized by CD4+ T Cells," *Journal of Experimental Medicine*, 195(11), pp. 1397-1406. (2002).
Wolfel, et al., "A p16INK4a-Insensitive CDK4 Mutant Targeted by Cytolytic T Lymphocytes in a Human Melanoma," *Science*, 269(5228), pp. 1281-1284. (1995).
Zhou, et al., "Diverse CD8+ T-Cell Responses to Renal Cell Carcinoma Antigens in Patients Treated with an Autologous Granulocyte-Macrophage Colony-Stimulating Factor Gene-Transduced Renal Tumor Cell Vaccine," *Cancer Research*, 65(3), pp. 1079-1088. (2005).
Zhou, et al., "Persistence of Multiple Tumor-Specific T-Cell Clones is Associated with Complete Tumor Regression in a Melanoma Patient Receiving Adoptive Cell Transfer Therapy," *Journal of Immunology*, 28, pp. 53-62. (2005). NIH Public Access Author Manuscript Retrieved from https://www.ncbi.nlm.nih.gov/pmc/articles/PMC2175172/pdf/nihms36125.pdf.
Extended European Search report issued in European Patent Application No. 16860902, dated Mar. 22, 2019.
Poznansky et al., "Efficient generation of human T cells from a tissue-engineered thymic organoid" *Nature Biology*, 2000, 18:729-734.
Themeli et al., "New Cell Sources for T Cell Engineering and Adoptive Immunotherapy," *Cell Stem Cell*, 2015, 16(4):357-366.
Yui et al., "Developmental gene networks: a triathlon on the course to T cell identity" *Nature Reviews Immunology*, 2014, 14(8):529-545.
Anderson et al., "Cellular Interactions in Thymocyte Development" *Annu Rev. Immunol.*, 1996, 14:73-99.
Awong et al., "Human CD8 T cells generated in vitro from hematopoietic stem cells are functionally mature" *BMC Immunol*, 2011, 12:22.
Chen et al., "NS21: re-defined and modified supplement B27 for neuronal cultures" *J. Neurosci Methods*, 2018, 171(2):239-247.
Chung et al., "Engineering the human thymic microenvironment to support thymopoiesis in vivo", *Stem Cells*, 32(9):2386-2396, (2014).
Dallas et al., "Density of the Notch Ligand Delta1 determines generations of B and T cell precursors from hematopoietic stem cells", *The Journal of Experimental Medicine*, 201(9):1361-1366, (2005).
De Smedt et al., "T-lymphoid differentiation potential measured in vitro is higher in CD34+CD38−/lo hematopoietic stem cells from umbilical cord blood than from bone marrow and is an intrinsic property of the cells" *Haematologica*, 2011, 96(5):646-654.
Evseenko et al., "Mapping the first stages of mesoderm commitment during differentiation of human embryonic stem cells" *Proc Natl Acad Sci U.S.A.*, 2010, 107(31):13742-7.
International Search Report and Written Opinion issued in International Application No. PCT/US2016/059375, dated Feb. 8, 2017.

La Motte-Mohs, "Induction of T-cell development from human cord blood hematopoietic stem cells by Delta-like 1 in vitro" *Blood*, 2005, 105(4):1431-1439.
Ludwig et al., "Derivation of human embryonic stem cells in defined conditions," *Nat Biotechnol*, 2006, 24(2):185-7.
Ludwig et al., "Feeder-independent culture of human embryonic stem cells," *Nat Methods*, 3(8):637-646.
Schmitt et al., "Induction of T Cell Development from Hematopoietic Progenitor Cells by Delta-like-1 In Vitro" *Immunity*, 2002, 17:749-756.
Seet et al., "Artificial Thymic Organoids permit Allelic Exclusion and Efficient Generation of Naive TCR-Engineered T-Cells from Human Hematopoietic Stem Cells In Vitro" *Blood*, 2016, 128:4553.
Snauwaert et al., "In vitro generation of mature, naive antigen-specific CD8+ T cells with a single T-cell receptor by agonist selection" *Leukemia*, 2014, 28:830-841.
Tebas et al., "Antiviral effects of autologous CD4 T cells genetically modified with a conditionally replicating lentiviral vector expressing long antisense to HIV", *Blood*, 121(9):1524-1533, (2013).
Van Coppernolle et al., "Functionally Mature CD4 and CD8 TCRαβ Cells are Generated in OP9-DL1 Cultures from Human CD34+ Hematopoietic Cells" *J. Immunol*, 2009, 183(8):4859-70.
Vatakis et al., "Introduction of exogenous T-cell receptors into human hematopoietic progenitors results in expclusion of endogenous T-cell receptor expression", *Molecular Therapy*, 21(5):1055-6063, (2013).
Itoh, K., et al., Reproducible Establishment of Hemopoietic Supportive Stromal Cell Lines from Murine Bone Marrow. Exp. Hematol., vol. 17, pp. 145-153 (1989).
Deniger, et al., "Bispecific T-Cells Expressing Polyclonal Repertoire of Endogenous γδ T-Cell Receptors and Introduced CD19-Specific Chimeric Antigen Receptor," *Molecular Therapy*, 21(3): 638-647, 2013.
Martin, et al., "Differences in Lymphocyte Developmental Potential Between Human Embryonic Stem Cell and Umbilical Cord Blood-Derived Hematopoietic Progenitor Cells," *Blood*, 112(7): 2730-2737, 2008.
Office Action Issued in Corresponding Japanese Patent Application No. 2018-522655, dated Nov. 30, 2020.
Office Action Issued in Eurasian Patent Application No. 201891059, dated Apr. 30, 2021.
Search Report Issued in Singapore Patent Application No. 11201803419P, dated Oct. 2, 2019.
Smith, et al., "Genetic Engineering of Hematopoietic Stem Cells to Generate Invariant Natural Killer T Cells," *PNAS*, 112(5): 1523-1528, 2015.
Viardot, et al., "Potential Antiinflammatory Role of Insulin Via the Preferential Polarization of Efffector T Cells Toward a T Helper 2 Phenotype," *Endocrinology*, 148(1): 346-353, 2007.
Written Opinion Issued in Singapore Patent Application No. 11201803419P, dated Oct. 16, 2019.
Yost, et al., "Defined, Serum-Free Conditions for In-Vitro Culture of Primary Human T-ALL Blasts," *Leukemia*, 27(6): 1437-1440, 2013.
Calvo, Julien et al., Assessment of Human Multi-Potent Hematopoietic Stem/Progenitor Cell Potential Using a Single In Vitro Screening System. *PLOS One*, vol. 7, Issue 11, pp. 1-12,2012).
Manning J., et al., Vitamins C Promotes Maturation of T-Cells. *Antioxidants & Redox Signaling*, vol. 19, No. 17, pp. 2054-2067 (2013).
Singapore Written Opinion dated Jul. 19, 2021 issued in Singapore Application No. 11201803419P.
Ellmeier et al., "Transcriptional control of CD4 and CD8 coreceptor expression during T cell development," *Cell. Mol. Life Sci.* 2013, 18 pages.
Ho et al., "CD4-CD8αα Subset of CD1d-Restricted NKT Cells Controls T Cell Expansion," *J Immunol* 2004; 172:7350-7358.
Office Action issued in Corresponding Eurasian Application No. 201891059, dated Mar. 28, 2022 (English Translation provided).

* cited by examiner

METHOD FOR GENERATING HUMAN DENDRITIC CELLS FOR IMMUNOTHERAPY

CROSS-REFERENCE TO RELATED APPLICATIONS

This application is a national phase application under 35 U.S.C. § 371 of International Application No. PCT/US2016/033339, filed on May 19, 2016, which claims benefit of and priority to USSN 62/164,368, filed on May 20, 2015, the contents of which applications are incorporated herein by reference in their entirety for all purposes.

STATEMENT OF GOVERNMENTAL SUPPORT

This invention was made with government support under Grant No. NIH T32HL066992 and NIH P01 HL073104 awarded by the National Institutes of Health. The Government has certain rights in this invention.

BACKGROUND

The use of dendritic cells (DCs) to present tumor-associated antigens to autologous T cells (so-called "dendritic cell vaccines" or "cancer vaccines") has been widely investigated as an approach to cancer immunotherapy, and has led to one FDA-approved therapy (sipuleucel-T). Overall, however, this approach has demonstrated only modest clinical efficacy, which may be due to multiple factors including DC-intrinsic properties, tumor antigen properties, activation of endogenous T cell checkpoints, and in vivo adaptive tumor responses (reviewed in Palucka and Banchereau (2012) *Nat. Rev. Cancer*, 12: 265-277). Of these, DC-intrinsic properties may present a critical initial barrier to developing effective DC vaccines, as adequate T cell priming is a requisite for subsequent efficacy.

A key determinant of DC-intrinsic properties is the source and type of DC used. Clinical DC vaccines have relied almost exclusively on monocyte-derived DC (MoDC, also known as "inflammatory DC"), which are typically CD14+ DC-SIGN+ antigen presenting cells generated from either blood monocytes or CD34+ HSPC by culture in stroma-free conditions in the presence of GM-CSF and IL-4, followed by "maturation" with pro-inflammatory stimuli such as interferon-gamma, TNF-alpha, LPS, or poly I:C. MoDC have several limitations: Firstly, they are relatively inefficient at cross-presenting cellular antigens to CD8+ T cells and priming cytotoxic T cell (CTL) responses, and thus must be loaded with exogenous peptides. This has required prior knowledge and synthesis of epitopes with HLA specificity, and depending on the peptide may restrict antigen presentation to an MHC class I context. Class I restriction may preclude induction of Th1/Th2 responses, which are required for durable cytotoxic and T memory responses in vivo. Furthermore, the requirement for exogenous peptide loading limits the use of MoDC vaccines to patients with HLA haplotypes for which there are known immunodominant HLA-binding peptide sequences. Electroporation of MoDCs with tumor-derived mRNA or mRNA encoding tumor associated antigens is an experimental approach to promote class and haplotype non-restricted antigen presentation; however this approach may still result in varying efficacy depending on the efficiency of mRNA transcription and antigen presentation via Class I and Class II pathways, and also comes at the cost of decreased cell viability due to electroporation. Finally, upon adoptive transfer, in vitro derived MoDCs are relatively inefficient at homing to secondary lymphoid organs (SLOs), which may critically limit their in vivo activity.

SUMMARY

In various embodiments methods of efficiently generating and/or expanding large number of human CLEC9A+ dendritic cells are provided. Additionally, in certain embodiments, CLEC9A+ dendritic cells and populations of CLEC9A+ dendritic cells produced by these methods are provided.

CLEC9A+ DCs are a naturally occurring type of DC that exhibits potent cross-presenting and CTL-priming ability, as well as the potential to elicit Th1 and Th2 T cell responses in vivo (reviewed in van der Aa et al. (2014) *Semin. Cell Dev. Biol.* PMID: 24910448; and Tullett et al. (2014) *Front Immunol.* 22(5): 239). These cell-intrinsic properties permit the processing and cross-presentation of global epitopes from intact tumor cells or tumor cell preparations, obviating the need for in vitro loading with defined HLA-targeted peptides or mRNA electroporation. It is believed that provision of large quantities of CLEC9A+ DCs as described herein permits the development of cancer "vaccines" without the need for identification and synthesis of tumor-specific epitopes. The CLEC9A+ DCs permit antigen processing and presentation via both MHC class I and class II pathways; and allow their use in patients of any HLA haplotype.

As naturally occurring CLEC9A+ DCs physiologically circulate in the blood and traffic to SLOs, it is believed the DCs generated as described herein will prove to be superior to MoDCs in homing to SLOs. Thus, using the methods described herein, CLEC9A+ DCs present a unique opportunity for developing better DC immunotherapies. It is believed that this has not previously been possible due to the rarity of CLEC9A+ DCs in the blood, and the inability in vitro to generate or expand sufficient quantities for use in human studies.

Various embodiments contemplated herein may include, but need not be limited to, one or more of the following:

Embodiment 1

A method of producing a cell population enriched for CLEC9A+ dendritic cells, said method comprising culturing stem cells and/or progenitor cells in a cell culture comprising: culture medium; and a notch ligand.

Embodiment 2

The method of embodiment 1, wherein said cell culture comprises stem cell factor (SCF).

Embodiment 3

The method according to any one of embodiments 1-2, wherein said cell culture comprises FLT3 ligand (FLT3L).

Embodiment 4

The method according to any one of embodiments 1-3, wherein said cell culture comprises thrombopoietin (TPO).

Embodiment 5

The method according to any one of embodiments 1-4, wherein said cell culture comprises IL-3 and/or GM-CSF.

Embodiment 6

The method according to any one of embodiments 1-5, wherein said notch ligand comprises a canonical notch ligand, or a fragment thereof.

Embodiment 7

The method of embodiment 6, wherein said canonical notch ligand is selected from the group consisting of Delta-like ligand 4 (DLL4), Delta-like ligand 1 (DLL1), Jagged 1 (JAG1), Jagged 2 (JAG2), Delta-like ligand 3 (DLL3), and X-delta 2.

Embodiment 8

The method of embodiment 7, wherein said canonical notch ligand is DLL4.

Embodiment 9

The method of embodiment 7, wherein said canonical notch ligand is DLL1.

Embodiment 10

The method of embodiment 1, wherein said notch ligand comprises a non-canonical notch ligand.

Embodiment 11

The method of embodiment 10, wherein said non-canonical notch ligand is selected from the group consisting of Contactin-1, NOV/CCN3, Contactin-6, Periostin/OSF-2, DLK2/EGFL9, Pref-1/DLK1/FA1, DNER, Thrombospondin-2, MAGP-1/MFAP2, Thrombospondin-3, MAGP-2/MFAP5, Thrombospondin-4, and Netrin-1.

Embodiment 12

The method according to any one of embodiments 1-11, wherein said stem cells and/or progenitor cells do not include human embryonic stem cells.

Embodiment 13

The method according to any one of embodiments 1-11, wherein said stem cells and/or progenitor cells comprise hematopoietic stem cell and/or progenitor cells (HSPCs).

Embodiment 14

The method of embodiment 13, wherein said cells comprise a cell population enriched for CD34+ cells.

Embodiment 15

The method according to any one of embodiments 13-14, wherein said cells are derived from bone marrow, umbilical cord, peripheral blood, or mobilized peripheral blood.

Embodiment 16

The method according to any one of embodiments 13-15, wherein said cells are not derived from human embryonic tissue.

Embodiment 17

The method according to any one of embodiments 1-11, wherein said stem cells and/or progenitor cells comprise stem cells.

Embodiment 18

The method of embodiment 17, wherein said stem cells comprise embryonic stem cells, adult stem cells, or induced pluripotent stem cells.

Embodiment 19

The method according to any one of embodiments 1-18, wherein said notch ligand is provided by co-culture with a stromal cell line, primary stromal and/or mesenchymal cells, or ES or iPSC-derived stromal/mesenchymal cells transfected with a nucleic acid construct that encodes and expresses said notch ligand.

Embodiment 20

The method of embodiment 19, wherein said nucleic acid construct encodes a mammalian notch ligand or a fragment thereof.

Embodiment 21

The method of embodiment 20, wherein said nucleic acid encodes a human or murine notch ligand or a fragment thereof.

Embodiment 22

The method according to any one of embodiments 19-21, wherein said notch ligand is provided by co-culture with a human or murine stromal cell line.

Embodiment 23

The method of embodiment 22, wherein said notch ligand is provided by co-culture a cell line selected from the group consisting of MS5, OP9, S17, HS-5, and HS-27A.

Embodiment 24

The method of embodiment 19, wherein said stroma cells comprise stem cells.

Embodiment 25

The method of embodiment 24, wherein said stroma cells comprise stem cells autologous to the source of said stem cells and/or progenitor cells.

Embodiment 26

The method according to any one of embodiments 24-25, wherein said stem cells are mesenchymal stem cells (MSCs).

Embodiment 27

The method of embodiment 24, wherein said stroma cells comprise induced pluripotent stem cells (IPSCs) or derivatives of IPSCs, or human embryonic stem cells.

Embodiment 28

The method of embodiment 27, wherein said stroma cells do not include human embryonic stem cells.

Embodiment 29

The method of embodiment 27, wherein said stroma cells comprise IPSCs or derivatives of IPSCs autologous to the source of said stem cells and/or progenitor cells.

Embodiment 30

The method according to any one of embodiments 1-18, wherein said notch ligand is provided as an immobilized ligand in the absence of stromal cells.

Embodiment 31

The method of embodiment 30, wherein said notch ligand is a mammalian notch ligand or a fragment thereof.

Embodiment 32

The method according to any one of embodiments 30-31, wherein said notch ligand is a human or murine notch ligand or a fragment thereof.

Embodiment 33

The method according to any one of embodiments 30-32, wherein said notch ligand is provided as a ligand attached to a surface in a cell culture vessel or attached to a bead or other solid substrate in said culture.

Embodiment 34

The method of embodiment 33, wherein said notch ligand is attached to a surface using fibronectin or other extracellular matrix protein/s.

Embodiment 35

The method according to any one of embodiments 1-34, wherein said cell culture medium comprises a medium selected from the group consisting of MEM (Minimal Essential Medium), DMEM (Dulbecco's Modified Eagle's Medium), BME (Basal Medium Eagle), RPMI 1640, DMEM/F-12 (Dulbecco's Modified Eagle's Medium: Nutrient Mixture F-12), DMEM/F-10 (Dulbecco's Modified Eagle's Medium: Nutrient Mixture F-10), α-MEM (α-Minimal essential Medium), G-MEM (Glasgow's Minimal Essential Medium), IMDM (Isocove's Modified Dulbecco's Medium), essential 8 (E8) medium, KnockOut DMEM, AIM V, X-VIVO-15, StemSpan, and CellGro Dendritic Cell Medium.

Embodiment 36

The method of embodiment 35, wherein said cell culture medium comprises MEM.

Embodiment 37

The method according to any one of embodiments 1-36, wherein said culture contains IL-3 and GMCSF.

Embodiment 38

The method according to any one of embodiments 1-36, wherein said culture contains IL-3, but not GMCSF.

Embodiment 39

The method according to any one of embodiments 1-36, wherein said culture contains GMCSF, but not IL-3.

Embodiment 40

The method according to any one of embodiments 1-39, wherein said culture does not contain IL-7.

Embodiment 41

The method according to any one of embodiments 1-40, wherein said medium is supplemented with L-alanyl-L-glutamine dipeptide.

Embodiment 42

The method of embodiment 41, wherein said L-alanyl-L-glutamine dipeptide is provided as GlutaMax.

Embodiment 43

The method according to any one of embodiments 1-42, wherein said culture comprises: MEM medium with L-alanyl-L-glutamine dipeptide (e.g., Glutamax); fetal calf serum or human AB serum; recombinant SCF; recombinant FLT3L; and IL-3 or GM-CSF.

Embodiment 44

The method of embodiment 43, wherein said culture comprises: about 5% human AB serum; about 5 ng/ml SCF; about 5 ng/ml FLT3L; and about 5 ng/ml IL-3 or about 10 ng/ml GM-CSF.

Embodiment 45

The method of embodiment 43, wherein said culture comprises: about 20% defined fetal calf serum; about 5 ng/ml SCF; about 5 ng/ml FLT3L;
and about 5 ng/ml IL-3 or about 10 ng/ml GM-CSF.

Embodiment 46

The method according to any one of embodiments 43-45, wherein said culture comprises TPO.

Embodiment 47

The method of embodiment 46, wherein said culture comprises about TPO at about 50 ng/mL.

Embodiment 48

The method according to any one of embodiments 1-47, wherein said method produces a cell population wherein CLEC9A+ cells comprise at least 10% of CD45+ cells in said culture, or at least 15% of CD45+ cells in said culture, or at least 20% of CD45+ cells in said culture, or at least 25% of CD45+ cells in said culture, or at least 30% of CD45+ cells in said culture, or at least 35% of CD45+ cells in said culture, or at least 40% of CD45+ cells in said culture, or at least 45% of CD45+ cells in said culture, or at least 50% of CD45+ cells in said culture, or at least 60% of CD45+ cells in said culture, or at least 70% of CD45+ cells in said culture, or at least 80% of CD45+ cells in said culture, or at least 85% of CD45+ cells in said culture, or about 90% of CD45+ cells in said culture.

Embodiment 49

The method of embodiment 48, wherein said method produces a cell population wherein CLEC9A+ cells comprise at least 85% of CD45+ cells in said culture.

Embodiment 50

The method according to any one of embodiments 1-49, wherein said method produces CLEC9A+ cells competent at cross-presenting antigen without adjuvant and/or without maturation.

Embodiment 51

The method of embodiment 50, wherein said method produces CLEC9A+ cells competent at cross-presenting antigen without adjuvant.

Embodiment 52

The method according to any one of embodiments 50-51, wherein said method produces CLEC9A+ competent at cross-presenting antigen without maturation.

Embodiment 53

The method of embodiment 50, wherein said method produces CLEC9A+ cells competent at cross-presenting without TLR ligand and/or polyI:C (TLR3 agonist).

Embodiment 54

The method according to any one of embodiments 1-53, wherein said method further comprises isolating CLEC9A+ cells from said culture.

Embodiment 55

The method of embodiment 54, wherein said isolating by a method selected from the group consisting of flow cytometry, or magnetic bead sorting, or affinity purification.

Embodiment 56

The method according to any one of embodiments 54-55, wherein said isolating utilizes an antibody that binds CLEC9A, CD141 (BDCA3), XCR1, NECL-2 (CADM1), or other markers present on CLEC9A+ DC.

Embodiment 57

A method of preparing a dendritic cell vaccine for a subject, said method comprising: preparing a cell population enriched for CLEC9A+ dendritic cells using the method according to any one of embodiments 1-56; and pulsing and/or loading said dendritic cells with a tumor cell antigen and/or a tumor cell lysate or tumor cell preparation.

Embodiment 58

The method of embodiment 57, wherein said method further comprises providing a maturation signal to said dendritic cells.

Embodiment 59

The method of embodiment 58, wherein said maturation signal comprises a TLR3 agonist.

Embodiment 60

The method of embodiment 59, wherein said TLR3 agonist comprises polyI:C.

Embodiment 61

The method according to any one of embodiments 58-60 wherein said maturation signal comprises a TLR8 agonist.

Embodiment 62

The method of embodiment 61, wherein said TLR8 agonist is selected from the group consisting of cpd14b (Kokatla et al. (2014) *Chem. Med. Chem.* 9: 719), imiquimod, N-{4-[4-amino-2-(2-methoxyethyl)-1H-imidazo[4,5-c]quinolin-1-yl]butyl}quinolin-3-carboxamide, N-{4-[4-amino-2-(2-methoxyethyl)-1H-imidazo[4,5-c]quinolin-1-yl]butyl}qui-noxaline-2-carboxamide, N-[4-(4-amino-2-propyl-1H-imidazo[4,5-c]quinolin-1-yl)butyl]morpholine-4-carboxamide, 2-propylthiazolo[4,5-c]quinolin-4-amine, $N^1$-[2-(4-amino-2-butyl-1H-imidazo[4,5-c][1,5]naphthridin-1-yl)ethyl]-2-amino-4-methylpentanamide, $N^1$-[2-(4-amino-1H-imidazo[4,5-c]quinolin-1-yl)butyl]-2-phenoxybenzamide, $N^1$-[2-(4-amino-2-butyl-1H-imidazo[4,5-c]quinolin-1-yl)ethyl]-1-propanesulfonamide, N-{2-[2-(4-amino-2-ethyl-1H-imidazo[4,5-c]quinolin-1-yl)ethyoxy]ethyl}-N'-phenylurea, 1-{4-[3,5-dichlorophenyl)thio]butyl}-2-ethyl-1H-imidazo[4,5-c]quinolin-4-amine, N-{2-[4-amino-2-(ethoxymethyl)-1H-imidazo[4,5-c]quinolin-1-yl]ethyl}-N'-(-3-cyanophenyl)urea, 4-amino-α, and α-dimethyl-2-methoxyethyl-1H-imidazo[4,5-c]quinoline-1-ethanol, 2-propylthiazolo-4,5-c]quinolin-4-amine.

Embodiment 63

The method according to any one of embodiments 57-62, wherein said method comprises pulsing and/or loading said dendritic cells with a tumor cell antigen selected from the group consist of WT1, MUC1, MP2, HPV E6 E7, EGFRvIII, HER-2/neu, diotype, MAGE A3, p53 nonmutant, NY-ESO-1, PSMA, GD2, CEA, MelanA/MART1, Ras mutant, gp100, p53 mutant, Proteinase3 (PR1), bcr-abl, Tyrosinase, Survivin, PSA, hTERT, Sarcoma translocation breakpoints, EphA2, PAP, ML-IAP, AFP, EpCAM, ERG (TMPRSS2 ETS fusion), NA17, PAX3, ALK, Androgen receptor, Cyclin B1, Polysialic acid, MYCN, RhoC, TRP-2, GD3, Fucosyl GM1, Mesothelin, PSCA, MAGE A1, sLe (animal), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-β, MAD-CT-2, and Fos-related antigen 1.

Embodiment 64

The method according to any one of embodiments 57-62, wherein said method comprises pulsing and/or loading said dendritic cells with a tumor cell neoantigen.

Embodiment 65

The method of embodiment 64, wherein said tumor cell neoantigen is encoded by a mutated gene selected from the group consisting of CDK4, MUM1, CTNNB1, CDC27, TRAPPC1, TPI, ASCC3, HHAT, FN1, OS-9, PTPRK, CDKN2A, HLA-A11, GAS7, GAPDH, SIRT2, GPNMB, SNRP116, RBAF600, SNRPD1, Prdx5, CLPP, PPP1R3B, EF2, ACTN4, ME1, NF-YC, HLA-A2, HSP70-2, KIAA1440, and CASP8.

Embodiment 66

The method according to any one of embodiments 57-62, wherein said method comprises pulsing and/or loading said dendritic cells with a lysate or tumor cell preparation from a cancer selected from the group consisting of acute lymphoblastic leukemia (ALL), acute myeloid leukemia (AML), Adrenocortical carcinoma, AIDS-related cancers (e.g., Kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CML), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sézary syndrome, skin cancer (e.g., melanoma, merkel cell carcinoma, basal cell carcinoma, nonmelanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

Embodiment 67

The method according to any one of embodiments 57-62, wherein said method comprises pulsing and/or loading said dendritic cells with a lysate or a tumor cell preparation from a cancer selected from the group consisting of ovarian cancer, lung cancer, breast cancer, bladder cancer, breast cancer (female-male), colon and rectal cancer, endometrial cancer, kidney cancer (renal cell and renal pelvis), leukemia (all types), lung cancer (including bronchus), melanoma, non-hodgkin lymphoma, pancreatic cancer, prostate cancer, and thyroid cancer.

Embodiment 68

The method according to any one of embodiments 57-62, wherein said method comprises pulsing and/or loading said dendritic cells with tumor antigen from a cancer selected from the group consisting of acute lymphoblastic leukemia (ALL), acute myeloid leukemia (AML), Adrenocortical carcinoma, AIDS-related cancers (e.g., Kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CML), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sézary syndrome, skin cancer (e.g., melanoma, merkel cell carcinoma, basal cell carcinoma, non-melanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

Embodiment 69

The method according to any one of embodiments 57-62, wherein said method comprises pulsing and/or loading said dendritic cells with tumor antigen from a cancer selected from the group consisting of ovarian cancer, lung cancer, breast cancer, bladder cancer, breast cancer (female-male), colon and rectal cancer, endometrial cancer, kidney cancer (renal cell and renal pelvis), leukemia (all types), lung cancer (including bronchus), melanoma, non-hodgkin lymphoma, pancreatic cancer, prostate cancer, and thyroid cancer.

Embodiment 70

The method according to any one of embodiments 57-69, wherein said CLEC9A+ cells are autologous to a subject to whom said vaccine is to be administered.

Embodiment 71

The method according to any one of embodiments 57-69, wherein said CLEC9A+ cells are heterologous to a subject to whom said vaccine is to be administered.

Embodiment 72

A dendritic cell vaccine, said vaccine comprising: a population of dendritic cells enriched for CLEC9A+ cells; where said cells are loaded with a tumor cell antigen and/or have been loaded during incubation with a tumor cell lysate or tumor cell preparation; and said cells are in a pharmaceutically acceptable carrier or excipient.

Embodiment 73

The vaccine of embodiment 72, wherein said excipient or carrier is suitable for parenteral administration to a human.

Embodiment 74

The vaccine according to any one of embodiments 72-73, wherein said vaccine is substantially sterile.

Embodiment 75

The vaccine according to any one of embodiments 72-74, wherein said cells are loaded with a tumor cell antigen selected from the group consist of WT1, MUC1, MP2, HPV E6 E7, EGFRvIII, HER-2/neu, diotype, MAGE A3, p53 nonmutant, NY-ESO-1, PSMA, GD2, CEA, MelanA/MART1, Ras mutant, gp100, p53 mutant, Proteinase3 (PR1), bcr-abl, Tyrosinase, Survivin, PSA, hTERT, Sarcoma translocation breakpoints, EphA2, PAP, ML-IAP, AFP, EpCAM, ERG (TMPRSS2 ETS fusion), NA17, PAX3, ALK, Androgen receptor, Cyclin B1, Polysialic acid, MYCN, RhoC, TRP-2, GD3, Fucosyl GM1, Mesothelin, PSCA, MAGE A1, sLe (animal), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-β, MAD-CT-2, and Fos-related antigen 1.

Embodiment 76

The vaccine according to any one of embodiments 72-74, wherein said cells are loaded with a tumor cell neoantigen.

Embodiment 77

The vaccine of embodiment 76, wherein said tumor cell neoantigen is encoded by a mutated gene selected from the group consisting of CDK4, MUM1, CTNNB1, CDC27, TRAPPC1, TPI, ASCC3, HHAT, FN1, OS-9, PTPRK, CDKN2A, HLA-A11, GAS7, GAPDH, SIRT2, GPNMB, SNRP116, RBAF600, SNRPD1, Prdx5, CLPP, PPP1R3B, EF2, ACTN4, ME1, NF-YC, HLA-A2, HSP70-2, KIAA1440, and CASP8.

Embodiment 78

The vaccine according to any one of embodiments 72-74, wherein said tumor antigen is from a cancer selected from the group consisting of acute lymphoblastic leukemia (ALL), acute myeloid leukemia (AML), Adrenocortical carcinoma, AIDS-related cancers (e.g., Kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CML), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sézary syndrome, skin cancer (e.g., melanoma, merkel cell carcinoma, basal cell carcinoma, non-melanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

Embodiment 79

The vaccine according to any one of embodiments 72-74, wherein said tumor antigen is from a cancer selected from the group consisting of ovarian cancer, lung cancer, breast cancer, bladder cancer, breast cancer (female-male), colon and rectal cancer, endometrial cancer, kidney cancer (renal cell and renal pelvis), leukemia (all types), lung cancer (including bronchus), melanoma, non-hodgkin lymphoma, pancreatic cancer, prostate cancer, and thyroid cancer.

Embodiment 80

The vaccine according to any one of embodiments 72-74, wherein said cells are loaded using a lysate from a cancer selected from the group consisting of acute lymphoblastic leukemia (ALL), acute myeloid leukemia (AML), Adrenocortical carcinoma, AIDS-related cancers (e.g., Kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CML), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sézary syndrome, skin cancer (e.g., melanoma, merkel cell carcinoma, basal cell carcinoma, nonmelanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

Embodiment 81

The vaccine according to any one of embodiments 72-74, wherein said cells are loaded using a lysate or cell preparation from a cancer selected from the group consisting of ovarian cancer, lung cancer, breast cancer, bladder cancer, breast cancer (female-male), colon and rectal cancer, endometrial cancer, kidney cancer (renal cell and renal pelvis), leukemia (all types), lung cancer (including bronchus), melanoma, non-hodgkin lymphoma, pancreatic cancer, prostate cancer, and thyroid cancer.

Embodiment 82

The vaccine according to any one of embodiments 72-81, wherein said CLEC9A+ cells are autologous to a subject to whom said vaccine is to be administered.

Embodiment 83

The vaccine according to any one of embodiments 72-81, wherein said CLEC9A+ cells are heterologous to a subject to whom said vaccine is to be administered.

Embodiment 84

The vaccine according to any one of embodiments 72-83, wherein said CLEC9A+ cells are competent at cross-presenting antigen without adjuvant and/or without maturation.

Embodiment 85

The vaccine of embodiment 84, wherein said CLEC9A+ cells are competent at cross-presenting antigen without adjuvant.

Embodiment 86

The vaccine according to any one of embodiments 84-85, wherein said CLEC9A+ cells are competent at cross-presenting antigen without maturation.

Embodiment 87

The vaccine of embodiment 84, wherein said CLEC9A+ cells are competent at cross-presenting without TLR ligand and/or polyI:C (TLR3 agonist).

Embodiment 88

A population of cells enriched for CLEC9A+ dendritic cells, wherein CLEC9A+ cells comprise at least 10% of CD45+ cells in said culture, or at least 15% of CD45+ cells in said population, or at least 20% of CD45+ cells in said population, or at least 25% of CD45+ cells in said population, or at least 30% of CD45+ cells in said population, or at least 35% of CD45+ cells in said population, or at least 40% of CD45+ cells in said population, or at least 45% of CD45+ cells in said population, or about 50% of CD45+ cells in said population, or at least 50% of CD45+ cells in said culture, or at least 60% of CD45+ cells in said culture, or at least 70% of CD45+ cells in said culture, or at least 80% of CD45+ cells in said culture, or at least 85% of CD45+ cells in said culture, or about 90% of CD45+ cells in said culture without cell sorting or immunoaffinity based purification; and/or a population of cells enriched for CLEC9A+ dendritic cells, wherein CLEC9A+ cells comprising said population are competent at cross-presenting antigen without adjuvant and/or without maturation.

Embodiment 89

The population of cells of embodiment 88, wherein CLEC9A+ cells comprise at least 85% of CD45+ cells in said culture.

Embodiment 90

The population of cells according to any one of embodiments 88-89, wherein CLEC9A+ cells comprising said population are competent at cross-presenting antigen without adjuvant.

Embodiment 91

The population of cells according to any one of embodiments 88-90, wherein CLEC9A+ cells comprising said population are competent at cross-presenting antigen without maturation.

Embodiment 92

The population of cells according to any one of embodiments 88-91, wherein said CLEC9A+ cells are competent at cross-presenting without TLR ligand and/or polyI:C (TLR3 agonist).

Definitions

The "canonical notch ligands" are characterized by extracellular domains typically comprising an N-terminal (NT) domain followed by a Delta/Serrate/LAG-2 (DSL) domain and multiple tandemly arranged Epidermal Growth Factor (EGF)-like repeats. The DSL domain together with the flanking NT domain and the first two EGF repeats containing the Delta and OSM-11-like proteins (DOS) motif are typically required for canonical ligands to bind Notch. The intracellular domains of some canonical ligands contain a carboxy-terminal PSD-95/Dlg/ZO-1-ligand (PDZL) motif that plays a role independent of Notch signaling. C. elegans DSL ligands lack a DOS motif but have been proposed to cooperate with DOS-only containing ligands to activate Notch signaling. Illustrative canonical notch ligands include, but are not limited to Delta-like ligand 4 (DLL4), Delta-like ligand 1 (DLL1), Jagged 1 (JAG1), Jagged 2 (JAG2), and the like.

"Non-canonical notch ligands" lack a DSL domain (Delta/Serrate/LAG-2), are structurally diverse and include integral- and GPI-linked membrane proteins as well as various secreted proteins.

Where a "notch ligand fragment" or a "canonical notch ligand fragment" is referenced herein, it is contemplated that the fragment is a fragment that binds notch.

"Toll-like receptor 3 agonists (TLR3 agonists)" are well known to those of skill in the art and include, but are not limited to isolated, naturally-occurring TLR3 agonists; and synthetic TLR3 agonists. TLR3 agonists isolated from a naturally-occurring source of TLR3 agonist are generally purified, e.g., the purified TLR3 agonist is at least about 80% pure, at least about 90% pure, at least about 95% pure, at least about 98% pure, at least about 99% pure, or more than 99% pure. Synthetic TLR3 agonists can be prepared by standard methods, and are generally at least about 80% pure, at least about 90% pure, at least about 95% pure, at least about 98% pure, at least about 99% pure, or more than 99% pure. TLR3 agonists include TLR3 agonists that are not attached to any other compound. TLR3 agonists include TLR3 agonists that are attached, covalently or non-covalently, to a second compound. In some embodiments, a TLR3 agonist is attached to another compound directly. In other embodiments, a TLR3 agonist is attached to another compound through a linker. In certain embodiments TLR3 agonists include naturally-occurring double-stranded RNA (dsRNA); synthetic ds RNA; and synthetic dsRNA analogs; and the like (Alexopoulou et al. (2001) Nature, 413: 732-738). An exemplary, non-limiting example of a synthetic ds RNA analog is poly(I:C). Other illustrative TLR3 agonists include, but are not limited to stathmin (see, e.g., U.S. Patent Pub. No: 2009/253622) and agonists described in PCT Publication No: WO 2012027017 A2, which is incorporated herein by reference for the TLR3 agonists described therein.

"Toll-like receptor 8 agonists (TLR8 agonists)" are well known to those of skill in the art and include, but are not limited to, compounds such as R-848, and derivatives and analogs thereof. Suitable TLR8 agonists include compounds having a 2-aminopyridine fused to a five membered nitrogen-containing heterocyclic ring. Such compounds include, for example, imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines. In one particular embodiment, the TLR8 agonist is an amide substituted imidazoquinoline amine. In certain embodiments, the TLR8 agonist is a sulfonamide substituted imidazoquinoline amine. In certain embodiments, the TLR8 agonist is a urea substituted imidazoquinoline amine. In certain embodiments, the TLR8 agonist is an aryl ether substituted imidazoquinoline amine. In certain embodiments, the TLR8 agonist is a heterocyclic ether substituted imidazoquinoline amine. In certain embodiments, the TLR8 agonist is an amido ether substituted imidazoquinoline amine. In certain embodiments, the TLR8 agonist is a sulfonamido ether substituted imidazoquinoline amine. In certain embodiments, the TLR8 agonist is a urea substituted imidazoquinoline ether. In certain embodiments, the TLR8 agonist is a thioether substituted imidazoquinoline amine. In certain embodiments, the TLR8 agonist is a 6-, 7-, 8-, or 9-aryl or heteroaryl substituted imidazoquinoline amine. In certain embodiments, the TLR8 agonist is an amide substituted tetrahydroimidazoquinoline amine. In certain embodiments, the TLR8 agonist is a sulfonamide substituted tetrahydroimidazoquinoline amine. In certain embodiments, the TLR8 agonist is a urea substituted tetrahydroimidazoquinoline amine. In certain embodiments, the TLR8 agonist is an aryl ether substituted tetrahydroimidazoquinoline amine. In certain embodiments, the TLR8 agonist is a heterocyclic ether substituted tetrahydroimidazoquinoline amine. In certain embodiments, the TLR8 agonist is an amido ether substituted tetrahydroimidazoquinoline amine. In certain embodiments, the TLR8 agonist is a sulfonamido ether substituted tetrahydroimidazoquinoline amine. In certain embodiments, the TLR8 agonist is a urea substituted tetrahydroimidazoquinoline ether. In certain embodiments, the TLR8 agonist is a thioether substituted tetrahydroimidazoquinoline amine. In certain embodiments, the TLR8 agonist is an amide substituted imidazopyridine amines. In certain embodiments, the TLR8 agonist is a sulfonamide substituted imidazopyridine amine. In certain embodiments, the TLR8 agonist is a urea substituted imidazopyridine amine. In certain embodiments, the TLR8 agonist is an aryl ether substituted imidazopyridine amine. In certain embodiments, the TLR8 agonist is a heterocyclic ether substituted imidazopyridine amine. In certain embodiments, the TLR8 agonist is an amido ether substituted imidazopyridine amine. In certain embodiments, the TLR8 agonist is a sulfonamido ether substituted imidazopyridine amine. In certain embodiments, the TLR8 agonist is a urea substituted imidazopyridine ether. In certain embodiments, the TLR8 agonist is a thioether substituted imidazopyridine amine. In certain embodiments, the TLR8 agonist is a 1,2-bridged imidazoquinoline amine. In certain embodiments, the TLR8 agonist is a 6,7-fused cycloalkylimidazopyridine amine. In certain embodiments, the TLR8 agonist is an imidazonaphthyridine amine. In certain embodiments, the TLR8 agonist is a tetrahydroimidazonaphthyridine amine. In certain embodiments, the TLR8 agonist is an oxazoloquinoline amine. In certain embodiments, the TLR8 agonist is a thiazoloquinoline amine. In certain embodiments, the TLR8 agonist is an oxazolopyridine amine. In certain embodiments, the TLR8 agonist is a thiazolopyridine amine. In certain embodiments, the TLR8 agonist is an oxazolonaphthyridine amine. In certain embodiments, the TLR8 agonist is a thiazolonaphthyridine amine. In yet certain embodiments, the TLR8 agonist is a 1H-imidazo dimer fused to a pyridine amine, quinoline amine, tetrahydroquinoline amine, naphthyridine amine, or a tetrahydronaphthyridine amine. In certain embodiments, the TLR8 agonist is a selective TLR8 agonist, e.g., the agonist modulates cellular activity through TLR8, but does not modulate cellular activity through TLR7. TLR8-selective agonists include those in U.S. Patent Publication 2004/0171086. Such TLR8 selective agonist compounds include, but are not limited to, the compounds shown in U.S. Patent Publication No. 2004/0171086 that include N-{4-[4-amino-2-(2-methoxyethyl)-1H-imidazo[4,5-c]quinolin-1-yl]butyl}quinolin-3-carboxamide, N-{4-[4-amino-2-(2-methoxyethyl)-1H-imidazo[4,5-c]quinolin-1-yl] butyl}qui-noxaline-2-carboxamide, and N-[4-(4-amino-2-propyl-1H-imidazo[4,5-c]quinolin-1-yl)butyl]morpholine-4-carboxamide. Other suitable TLR8-selective agonists include, but are not limited to, 2-propylthiazolo[4,5-c]quinolin-4-amine (U.S. Pat. No. 6,110,929); N.sup.1-[2-(4-amino-2-butyl-1H-imidazo[4,5-c][1,5]naphthridin-1-yl) ethyl]-2-amino-4-methylpentanamide (U.S. Pat. No. 6,194, 425); N.sup.1-[4-(4-amino-1H-imidazo[4,5-c]quinolin-1-yl) butyl]-2-phenoxy-benza-mide (U.S. Pat. No. 6,451,810); N.sup.1-[2-(4-amino-2-butyl-1H-imidazo[4,5-c]quinolin-1-yl)ethyl]-1-propane sulfon amide (U.S. Pat. No. 6,331,539); N-{2-[2-(4-amino-2-ethyl-1H-imidazo[4,5-c]quinolin-1-yl) ethyoxy]ethyl}-N'-phenylurea (U.S. Patent Publication 2004/0171086); 1-{4-[3,5-dichlorophenyl)thio]butyl}-2-ethyl-1H-imidazo[4,5-c]quinolin-4-amine (U.S. Patent Publication 2004/0171086); N-{2-[4-amino-2-(ethoxymethyl)-1H-imidazo[4,5-c]quinolin-1-yl]ethyl}-N'-(-3-cyanophenyl)urea (WO 00/76518 and U.S. Patent Publication No. 2004/0171086); and 4-amino-.alpha.,.alpha.-dimethyl-2-methoxyethyl-1H-imidazo[4,5-c]quinoline-1-ethanol (U.S. Pat. No. 5,389,640). Included for use as TLR8-selective agonists are the compounds in U.S. Patent Publication No. 2004/0171086. Also suitable for use is the compound 2-propylthiazolo-4,5-c]quinolin-4-amine.

DETAILED DESCRIPTION

Figure 1:
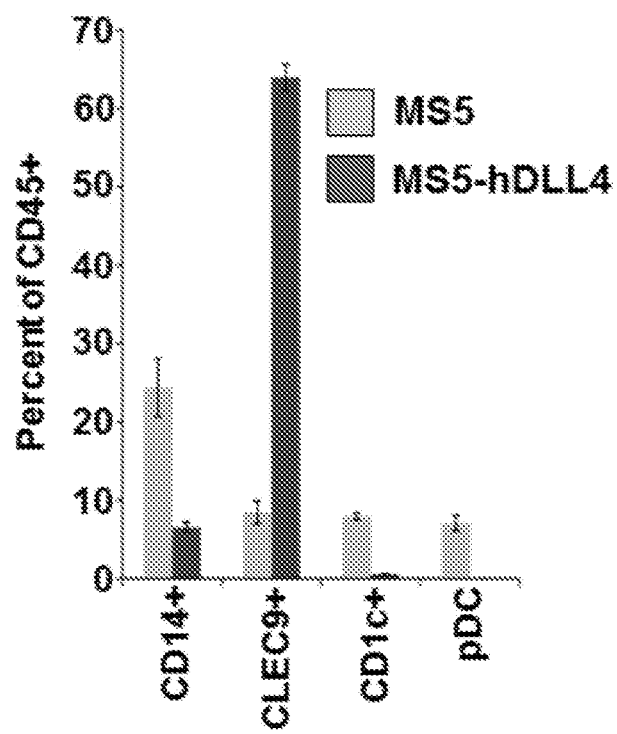
FIG. 1 shows that differentiation of CLEC9A+ DC from human cord blood CD34+ HSPCs is enhanced by presentation of the notch ligand DLL4 on MS5 stroma. Shown is data from cells harvested after 15 days of co-culture on MS5 or MS5-hDLL4 stromal cell monolayers in MEMα20% FBS with 5 ng/ml SCF, 5 ng/ml FLT3L, 50 ng/ml TPO, and 10 ng/ml GM-CSF. CD14+ monocytes, CD1c+ DC, and plasmacytoid DC (pDC) are shown for comparison. Frequencies are shown as a percentage of total CD45+ cells isolated from cultures. Error bars represent standard deviation of triplicate cultures wells.

In various embodiments methods of efficiently generating and/or expanding large number of human CLEC9A+ dendritic cells are provided. Additionally, in certain embodiments, CLEC9A+ dendritic cells and populations of CLEC9A+ dendritic cells produced by these methods are provided. In certain embodiments CLEC9A+ dendritic cells loaded and/or pulsed with particular antigens (e.g., tumor antigens) or with, inter alia, tumor lysates or tumor cell preparations are provided. In certain embodiments the CLED9A+ DCs provide effective tumor vaccines. The cells also find utility in a number of other contexts including, but not limited to regulating immune/autoimmune responses, inhibiting graft versus host disease, and the like.

CLEC9A+ DC are specialized antigen-presenting cells normally present in the human blood, lymph nodes, spleen, and other organs. They are also known as BDCA3+DC, CD141+ DC, XCR1+ DC, or BATF3+ DC, and can be identified based on high mRNA or protein expression of CLEC9A, CD141 (BDCA3/thrombomodulin), XCR1, BATF3, CADM1 (NECL2), TLR3, or IDO1 (reviewed in Vander Aa, et al. 2014).

CLEC9A+ DC are efficient at cross-presenting antigens from cellular sources to T cells, and thus are likely involved in regulating immune responses to pathogens, anti-tumor immunity and, in certain clinical settings, autoimmunity, transplant rejection, and graft versus host disease (reviewed in Tullett et al. (2014) *Front Immunol.* 22(5): 239). They are also present in the human thymus where they may be involved in the negative selection of self-reactive thymocytes and/or generation of regulatory T cells (Lei et al. (2011) *J Exp. Med.* 208(2): 383-394). The ability to generate large numbers of CLEC9A+ DC, as described herein, is believed to permit the development of immunotherapies for the treatment of a wide range of diseases and other pathologies.

In various embodiments the methods described here provide in vitro cell culture methods that use a Notch ligand to generate and expand large numbers of human CLEC9A+ DC from hematopoietic (or other) stem and/or progenitor cells (HSPC). Culture of HSPC in these conditions results in an inhibition of myeloid cell generation and selective generation/expansion of CLEC9A+ DC.

While the methods are described herein primarily with respect to hematopoietic stem and/or progenitor cells, it is believed that the methods can be utilized to expand/generate CLEC9A+ dendritic cells from numerous other sources, e.g., from embryonic stem cells, induced pluripotent stem cells (IPSCs), malignant hematopoietic cells, and the like.

In certain embodiments illustrative, but non-limiting embodiments, the methods involve comprising culturing stem cells and/or progenitor cells in a cell culture comprising culture medium, one or more notch ligands; stem cell factor (SCF); FLT3 ligand (FLT3L); and IL-3 and/or GMCSF.

Various culture media can be utilized. Illustrative, but non-limiting culture media include, but are not limited to MEM (Minimal Essential Medium), DMEM (Dulbecco's Modified Eagle's Medium), BME (Basal Medium Eagle), RPMI 1640, DMEM/F-12 (Dulbecco's Modified Eagle's Medium: Nutrient Mixture F-12), DMEM/F-10 (Dulbecco's Modified Eagle's Medium: Nutrient Mixture F-10), α-MEM (α-Minimal essential Medium), G-MEM (Glasgow's Minimal Essential Medium), IMDM (Isocove's Modified Dulbecco's Medium), essential 8 (E8) medium, KnockOut DMEM, AIM V, X-VIVO-15, StemSpan, CellGro Dendritic Cell Medium and the like.

The cells are cultured with one or more notch ligands which can include canonical notch ligands (e.g., Delta-like ligand 4 (DLL4), Delta-like ligand 1 (DLL1), Jagged 1 (JAG1), Jagged 2 (JAG2), Delta-like ligand 3 (DLL3), and X-delta 2, and the like) and/or one or more non-canonical notch ligands (e.g., Contactin-1, NOV/CCN3, Contactin-6, Periostin/OSF-2, DLK2/EGFL9, Pref-1/DLK1/FA1, DNER, Thrombospondin-2, MAGP-1/MFAP2, Thrombospondin-3, MAGP-2/MFAP5, Thrombospondin-4, Netrin-1, and the like).

In certain embodiments the notch ligand(s) are provided by co-culture with human or murine stromal cells that express the notch ligand(s). In certain embodiments the stromal cells comprise cells of a human or murine stromal cell line (e.g. MS5, OP9, S17, HS-5, HS-27A) or human stromal/mesenchymal cells (primary or derived from ES or iPSCs) transduced or transfected with the cDNA or mRNA for a human or murine Notch ligand.

In certain embodiments the notch ligand can be provided as a ligand immobilized on a surface in the cell culture (e.g., on a surface of the culture vessel, attached to beads, and the like). In certain embodiments, particularly where the notch ligand is provided immobilized on a surface, the stromal cells may be omitted.

In one illustrative, but non-limiting embodiments, optimized culture conditions are MEMα with Glutamax, 20% defined fetal calf serum, 5 ng/ml SCF, 5 ng/ml FLT3L, and 5 ng/ml IL-3 or 10 ng/ml GM-CSF, however variations of these culture conditions are also effective, e.g. serum free conditions, substitution for human serum, minimal cytokine conditions, etc.).

The stem and/or progenitor cells used in the methods described herein, can be provided using any of a number of methods known to those of skill in the art. In certain embodiments the cells are obtained from a commercial provider. In certain embodiments the cells are derived from a host to whom the CLEC9A+ cells are to be administered. In certain embodiments illustrative, but non-limiting embodiments, the starting cells may be an enriched HSPC population (e.g. defined as CD34+, CD34+ lineage−, or lineage−) or fractions thereof, including hematopoietic stem cells or hematopoietic progenitor cell populations. In certain embodiments illustrative, but non-limiting embodiments, the source of HSPC can be bone marrow, umbilical cord blood, peripheral blood, or mobilized peripheral blood (e.g. following treatment with G-CSF) from an autologous or allogeneic donor, depending on the clinical setting.

The above-described methods produce a population of cells highly enriched for CLEC9A+ cells. In certain embodiments the CLEC9A+ DCs are identified and/or isolated from the culture system. This is achieved through commercially available immunological methods, such as flow cytometry, magnetic-bead based cell sorting, and the like. CLEC9A+ DC may readily be identified or isolated based on binding of one or more commercially available antibody clones which recognize CLEC9A, CD141 (BDCA3), XCR1, NECL-2 (CADM1), or other markers present on CLEC9A+ DC.

In certain embodiments, the CLEC9A+ dendritic cells are loaded with and/or pulsed with tumor antigen, and/or tumor lysates or tumor cell preparations to produce an anti-cancer "vaccine". Illustrative tumor antigens for use in dendritic cell vaccine(s) include, but are not limited WT1, MUC1, MP2, HPV E6 E7, EGFRvIII, HER-2/neu, diotype, MAGE A3, p53 nonmutant, NY-ESO-1, PSMA, GD2, CEA, MelanA/MART1, Ras mutant, gp100, p53 mutant, Proteinase3 (PR1), bcr-abl, Tyrosinase, Survivin, PSA, hTERT, Sarcoma translocation breakpoints, EphA2, PAP, ML-IAP, AFP, EpCAM, ERG (TMPRSS2 ETS fusion), NA17, PAX3, ALK, Androgen receptor, Cyclin B1, Polysialic acid, MYCN, RhoC, TRP-2, GD3, Fucosyl GM1, Mesothelin, PSCA, MAGE A1, sLe (animal), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-β, MAD-CT-2, Fos-related antigen 1, and the like (see, e.g., Cheever et al. (2009) *Clin. Cancer Res.,* 15(17): 5323-5337; Palucka and Banchereau (2012) *Nat. Rev. Cancer,* 12: 265-277).

In certain embodiments, the CLEC9A+ dendritic cells are loaded with and/or pulsed with tumor neoantigens. Neoantigens are antigens encoded by tumor-specific mutated genes antigen. In particular tumor-specific neoantigens, typically arise via mutations that alter amino acid coding sequences (non-synonymous somatic mutations). Some of these mutated peptides can be expressed, processed and presented on the cell surface, and subsequently recognized by T cells. Because normal tissues do not possess these somatic mutations, neoantigen-specific T cells are not subject to central and peripheral tolerance, and also lack the ability to induce normal tissue destruction. As a result, neoantigens appear to represent ideal targets for cancer immunotherapy. Tumor cell neoantigens are well known to those of skill in the art (see, e.g., Lu and Robbins (2016) *Seminars Immunol.,* 28(1): 22-27), and an illustrative, but non-limiting list of neoantigens is shown in Table 1.

TABLE 1

Illustrative, but non-limiting human neoantigens.

| Cancer type | Mutated gene name | Reference |
|---|---|---|
| Melanoma | CDK4 | Wolfel et al. (1995) *Science*, 269: 1281-1284 |
| Melanoma | MUM1 | Coulie et al. (1995) *Proc. Natl. Acad. Sci. USA*, 92: 7976-7980 |
| Melanoma | CTNNB1 | Robbins et al. (1996) *J. Exp. Med.*, 183: 1185-1192 |
| Melanoma | CDC27 | Wang et al. (1999) *Science*, 284: 1351-1354 |
| Melanoma | TRAPPC1 | Chiari et al. (1999) *Cancer Res.*, 59: 5785-5792 |
| Melanoma | TPI | Pieper et al. (1999) *J. Exp. Med.*, 189: 757-766 |
| Melanoma | ASCC3 | Baurain et al. (2000) *J. Immunol.*, 164: 6057-6066 |
| Melanoma | HHAT | Kawakami et al. (2001) *J. Immunol.*, 166: 2871-2877 |
| Melanoma | FN1 | Wang et al. (2002) *J. Exp. Med.*, 195: 1397-1406 |
| Melanoma | OS-9 | Vigneron et al. (2002) *Cancer Immunity*, 2: 9 |
| Melanoma | PTPRK | Novellino et al. (2003) *J. Immunol.*, 170: 6363-6370 |
| Melanoma | CDKN2A, HLA-A11 | Huang et al. 92005) *J. Immunol.* 172: 6057-6064 |
| Melanoma | GAS7, GAPDH | Zhou et al. (2005) *J. Immunother.*, 28: 53-62 |
| Melanoma | SIRT2, GPNMB, SNRP116, RBAF600, SNRPD1 | Lennerz et al. (2005) *Proc. Natl. Acad. Sci. USA*, 102: 16013-16018 |
| Melanoma | Prdx5 | Sensi et al. (2005) *Cancer Res.* 65: 632-640 |
| Melanoma | CLPP | Corbiere et al. (2011) *Cancer Res.*, 71: 1253-1262 |
| Melanoma | PPP1R3B | Lu et al. (2013) *J. Immunol.*, 190: 6034-6042 |
| Lung cancer | EF2 | Hogan et al. (1998) *Cancer Res.*, 58: 5144-5150 |
| Lung cancer | ACTN4 | Echchakir et al. (2001) *Cancer Res.* 61: 4078-4083 |
| Lung cancer | ME1 | Karanikas et al. (2001) *Cancer Res.*, 61: 3718-3724 |
| Lung Cancer | NF-YC | M et al. (2006) *Int. J. Cancer*, 118: 1992-1997 |
| Renal cancer | HLA-A2 | Brandle et al. (1996) *J. Exp. Med.*, 183: 2501-2508 |
| Renal cancer | HSP70-2 | Gaudin et al. (1999) *J. Immunol.*, 162: 1730-1738 |
| Renal cancer | KIAA1440 | Zhou et al. (2005) *Cancer Res.*, 65: 1079-1088 |
| Head and neck squamous cell carcinoma | CASP8 | Mandruzzato et al.(1997) *J. Exp. Med.*, 186: 785-793 |

Where the DCs are to be pulsed with (e.g., cultured with) a tumor lysate or tumor cell preparation, illustrative but non-limiting tumor/cancer types include acute lymphoblastic leukemia (ALL), acute myeloid leukemia (AML), Adrenocortical carcinoma, AIDS-related cancers (e.g., Kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CML), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sézary syndrome, skin cancer (e.g., melanoma, merkel cell carcinoma, basal cell carcinoma, nonmelanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, Wilm's tumor, and the like.

Methods of pulsing DCs with tumor lysate are known to those of skill in the art (see, e.g., Lawman and Lawman (eds.), Cancer Vaccines: Methods and Protocols, Methods in Molecular Biology, vol. 1139, DOI 10.1007/978-1-4939-0345-0, Springer, New York (2014)).

The foregoing methods are intended to be illustrative and not limiting. Using the teachings provided herein numerous methods of generating/expanding CLEC9A+ dendritic cells, CLEC9A+ dendritic cell populations, and modified CLEC9A+ dendritic cells will be available to one of skill in the art.

EXAMPLES

The following examples are offered to illustrate, but not to limit the claimed invention.

Example 1

Generation and Expansion of CLEC9A+ Dendritic Cells from Human Bone Marrow CD34+ Cells Using a Notch Ligand We have found that $CD34^+$ hematopoietic stem and progenitor cells (HSPC) cultured in the presence of hematopoietic cytokines and a Notch ligand results in cultures that are highly enriched for CLEC9A+ dendritic cells (DC). We show here a representative experiment using primary human bone marrow CD34+ HSPCs cultured on MS5 stromal cells transduced with human DLL4 in the presence of SCF, FLT3L and either GM-CSF or IL-3. Culture of HSPCs for 14 days under these conditions resulted in cultures of CD45+ hematopoietic cells containing 19% and 30% $CLEC9A^+$ $CD141^+$ DC, respectively, whereas control cultures on MS5 cells not transduced with DLL4 generated 2-3% $CLEC9A^+$ DC. We conclude that culture of human HSPCs in the presence of a Notch ligand plus SCF, FLT3L, and IL-3 or GM-CSF is an efficient method for differentiating and expanding $CLEC9A^+$ DC.

Materials and Methods

Isolation of BM CD34+ HSPC

Bone marrow aspirates were obtained from healthy donors. Mononuclear cells were isolated by density centrifugation on Ficoll-Paque (GE Healthcare) per the manufacturer's protocol. $CD34^+$ HSPCs were magnetically isolated using the CD34 Ultrapure Kit and a MACS LS column (Miltenyi) per the manufacturer's protocol.

Stromal Cell Line Expressing DLL4

Full-length human DLL4 was cloned from a universal human RNA preparation (Agilent) by RT-PCR and ligated into pCCL-c-MNDU3-x-IRES-GFP at the EcoRl site. Lentiviral supernatant was prepared by co-transfection of 293T cells with the DLL4 vector, pCMV-ΔR8.9, and pCAGGS-VSV-G using TransIT 293T (Mirus). Supernatants were harvested at 48h and concentrated using an Amicon 100K filter (Millipore). Concentrated supernatant was used to infect MS5 murine bone marrow stromal cells. $GFP^{hi}$ cells were sorted at 72h (MS5-hDLL4, hereafter).

Co-Cultures to Generate CLEC9A+ DC

MS5-hDLL4 cells were plated at $8-9\times10^3$ cells per well of a 96-well plate the day before HSPC co-culture. For HSPC co-cultures, supernatant was aspirated from MS5-hDLL4 cells, and purified HSPCs were added at $5\times10^3$ cells per well in 200 µl MEM-alpha with Glutamax (Life Technologies) supplemented with 20% fetal calf serum (HyClone), recombinant human SCF (5 ng/ml), FLT3L (5 ng/ml), and either IL-3 (5 ng/ml) or GM-CSF (10 ng/ml) (all from Peprotech). Cells were incubated at 37° C./5% $CO_2$ for 15 days, during which half the media volume was replaced every 3-4 days with fresh media containing a 2× concentration of cytokines. At day 15, cells were harvested by pipetting, and analyzed by flow cytometry using the following antibody clones: CD45 (HI30), CLEC9A (8F9), CD141 (M80), CD14 (M5E2). $CLEC9A^+$ DC were defined as $CD45^+$ $CD14^-$ $CD141^+$ $CLEC9A^+$.

Results

Figure 2:
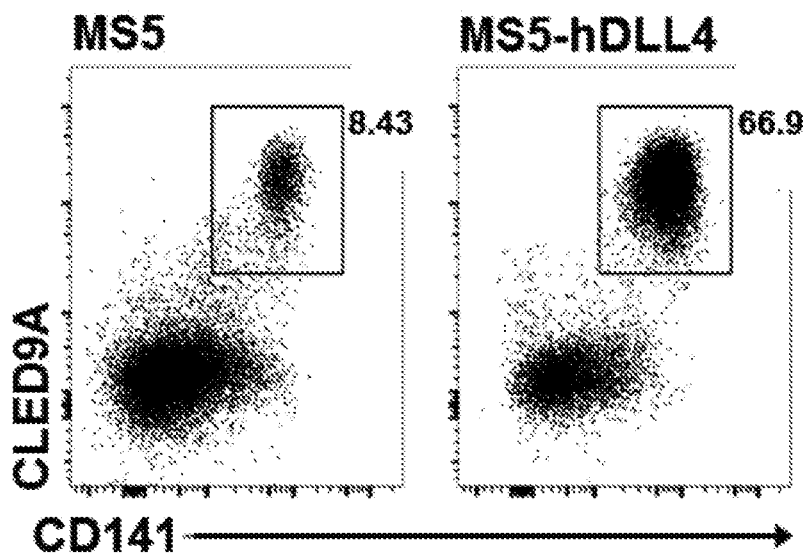
FIG. 2 shows representative flow cytometry plots from day 15 cultures as shown in FIG. 1), gated on total CD45+ cells. CLEC9A+ DC are gated based on co-expression of CLEC9A and CD141 (BDCA-3).
Figure 3:
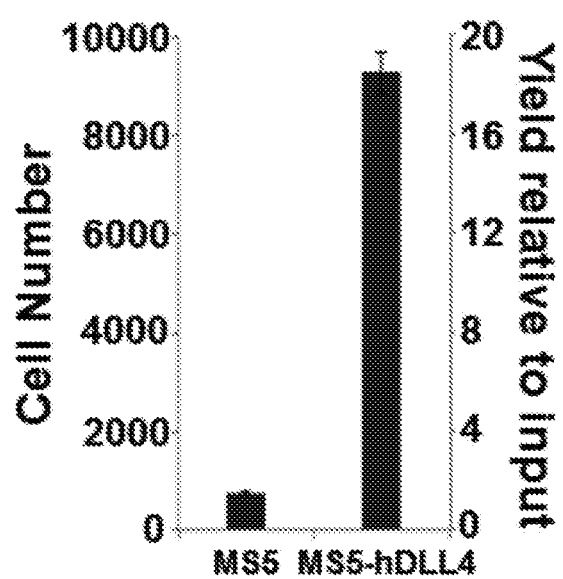
FIG. 3 shows CLEC9A+ DC yield from day 15 cultures, as shown in FIG. 1), expressed as absolute number of CLEC9A+ DC per well on day 15 (seeded on day 0 with 5,000 CD34+ cells per well); and as CLEC9A+ DC yield relative to input number of CD34+ cells.
Figure 4:
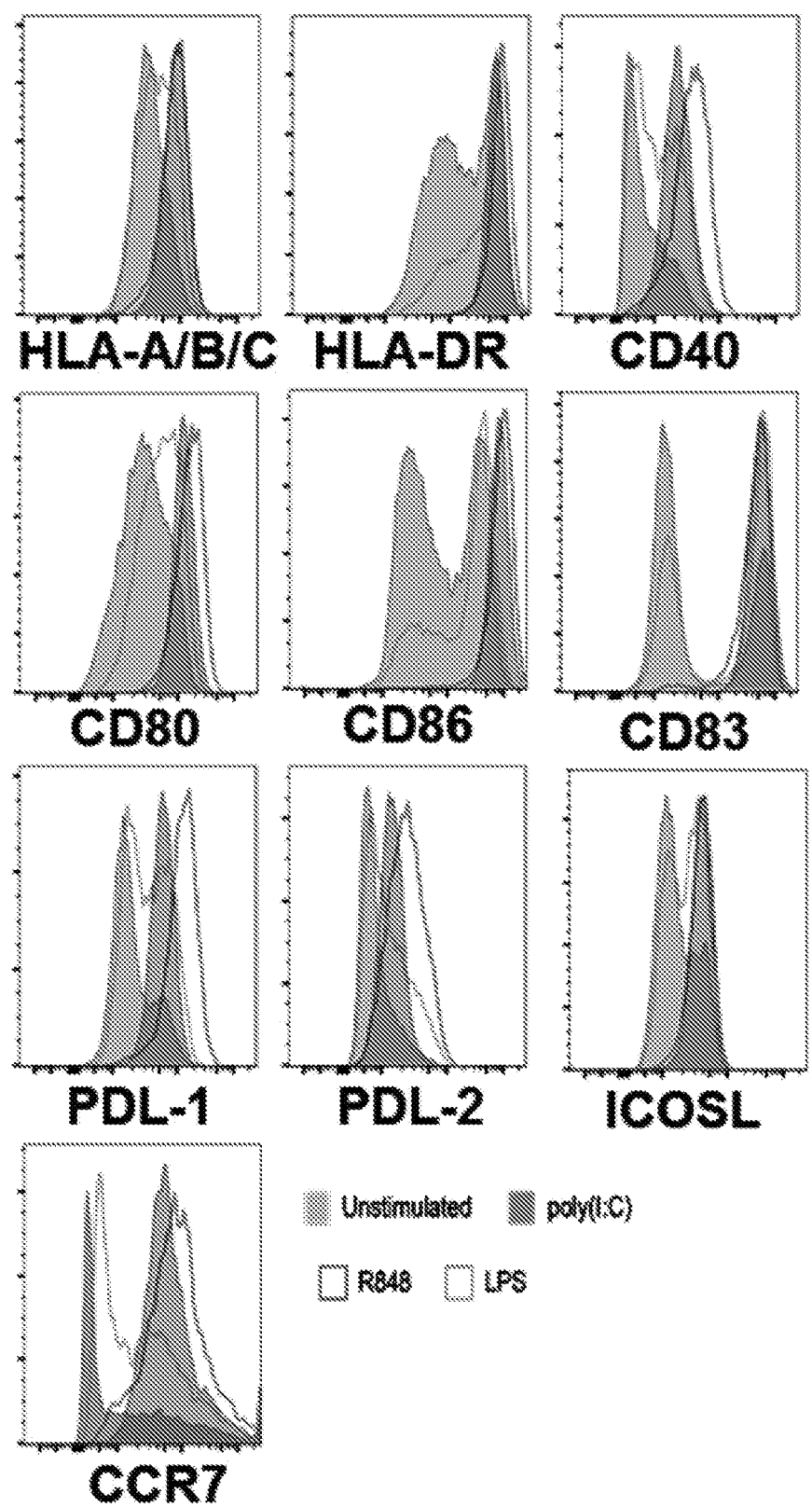
FIG. 4 shows basal and induced levels of co-stimulatory, co-inhibitory, and chemokine receptors on CLEC9A+ DC isolated from day 15 CB CD34+MS5-hDLL4 cultures and stimulated for 12h with the indicated ligands for TLR3, TLR8, or TLR4 (poly(I:C), R848, or LPS, respectively vs. unstimulated).
Figure 5:
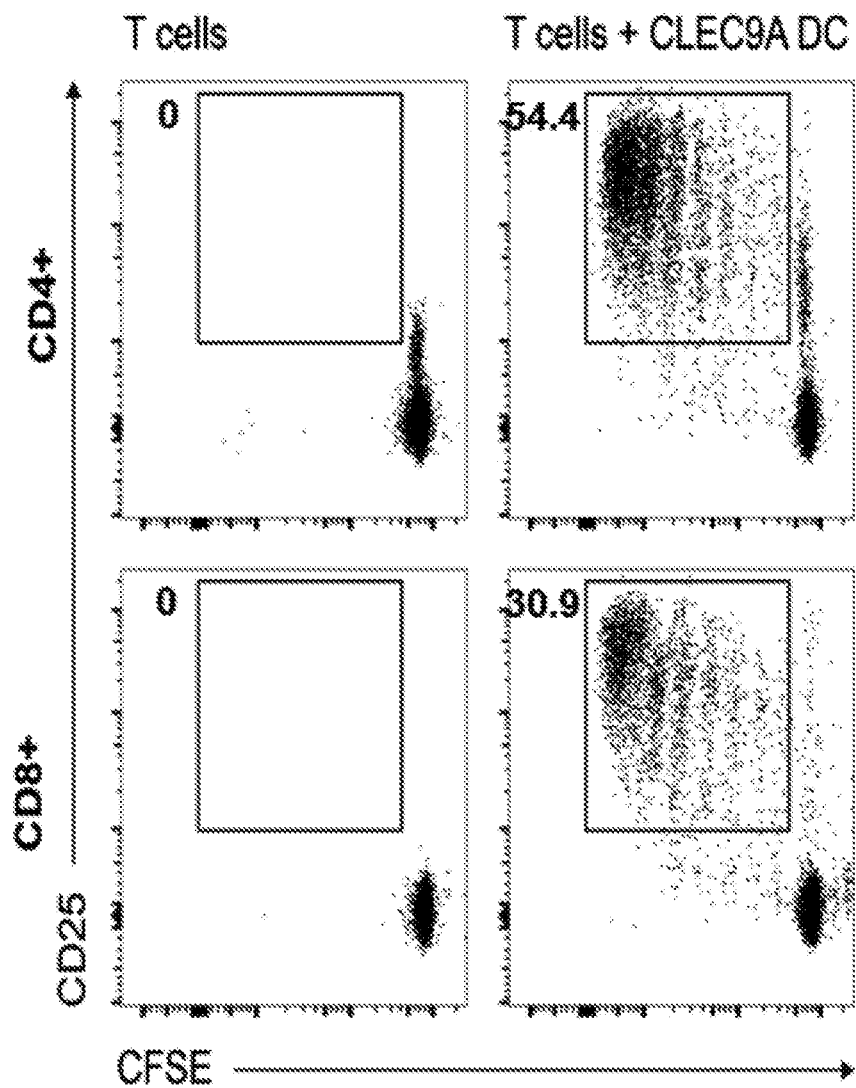
FIG. 5 shows the capacity of in vitro differentiated CLEC9A+ DC to activate T cells. CLEC9A+ DC generated in CB CD34+MS5-hDLL4 cultures were isolated from stromal cultures and co-cultured with CFSE-labeled allogeneic naïve T cells in a 1:5 DC:T ratio for 5 days. CELC9A+ DCs were not treated with maturation stimuli prior to or during assay. Plots are gated on CD3+CD4+ or CD3+CD8+ responder T cells.

Culture of CB $CD34^+$ HSPCs for 15 days on MS5-hDLL4 with SCF, FLT3L, and GM-CSF resulted in cultures of CD45+ hematopoietic cells containing around 67% $CLEC9A^+$ $CD141^+$ DC, whereas control cultures on MS5 cells not transduced with DLL4 generated around 8% $CLEC9A^+$ DC (FIGS. 1-5).

CONCLUSIONS

Ex vivo culture of $CD34^+$ HSPCs with stromal cells expressing the Notch ligand DLL4 in the presence of SCF, FLT3L, and IL-3 or GM-CSF is a novel method for the generation and expansion of $CLEC9A^+$ DC.

REFERENCES

La Motte-Mohs R N, Herer E, Zufiiga-Pflucker J C. Induction off-cell development from human cord blood hematopoietic stem cells by Delta-like 1 in vitro. Blood. 2005 Feb. 15; 105(4):1431-9. Epub 2004 Oct. 19.

Lee J, Breton G, Oliveira T Y, Zhou Y J, Aljoufi A, Puhr S, Cameron M J, Sekaly R P, Nussenzweig M C, Liu K. Restricted dendritic cell and monocyte progenitors in human cord blood and bone marrow. J Exp Med. 2015 Mar. 9; 212(3):385-99. doi: 10.1084/jem.20141442. Epub 2015 Feb. 16.

Ohishi K, Varnum-Finney B, Serda R E, Anasetti C, Bernstein I D. The Notch ligand, Delta-1, inhibits the differentiation of monocytes into macrophages but permits their differentiation into dendritic cells. Blood. 2001 Sep. 1; 98(5):1402-7. PMID: 11520788

Olivier A, Lauret E, Gonin P, Galy A. The Notch ligand delta-1 is a hematopoietic development cofactor for plasmacytoid dendritic cells. Blood. 2006 Apr. 1; 107(7): 2694-701. Epub 2005 Dec. 15.

Poulin L F, Salio M, Griessinger E, Anjos-Afonso F, Craciun L, Chen J L, Keller A M, Joffre 0, Zelenay S, Nye E, LeMoine A, Faure F, Donckier V, Sancho D, Cerundolo V, Bonnet D, Reise Sousa C. Characterization of human DNGR-1+BDCA3+ leukocytes as putative equivalents of mouse CD8alpha+ dendritic cells J Exp Med. 2010 Jun. 7; 207(6):1261-71. PMID: 20479117.

Proietto A I, Mittag D, Roberts A W, Sprigg N, Wu L. The equivalents of human blood and spleen dendritic cell subtypes can be generated in vitro from human CD34(+) stem cells in the presence of fms-like tyrosine kinase 3 ligand and thrombopoietin. Cell Mollmmunol. 2012 November; 9(6):446-54. PMID: 23085949.

Thordardottir S, Hangalapura B N, Hutten T, Cossu M, Spanholtz J, Schaap N, Radstake T R, vanderVoort R, Dolstra H. The aryl hydrocarbon receptor antagonist StemRegenin 1 promotes human plasmacytoid and myeloid dendritic cell development from CD34 hematopoietic progenitor cells. Stem Cells Dev. 2014 May 1; 23(9):955-67. PMID: 24325394.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of producing a cell population enriched for CLEC9A+ dendritic cells in a cell culture comprising culture medium, said method comprising co-culturing stem cells and/or progenitor cells with a human or murine stromal cell line transduced or transfected with a nucleic acid that encodes and expresses a notch ligand, wherein the notch ligand is DLL4, DLL1, Jagged 1 (JAG1), or Jagged 2 (JAG2), or a Notch-binding fragment of DLL4, DLL1, Jagged 1 (JAG1), or Jagged 2 (JAG2), wherein said culture medium is supplemented with L-alanyl-L-glutamine dipeptide.

2. The method of claim 1, wherein said cell culture comprises one or more of stem cell factor (SCF), FLT3 ligand (FLT3L), thrombopoietin (TPO), IL-3 and GM-CSF.

3. The method of claim 2, wherein said cell culture comprises: SCF, FLT3L, and IL-3 or GM-CSF.

4. The method of claim 1, wherein said stem cells and/or progenitor cells comprise hematopoietic stem cell and/or progenitor cells (HSPCs), and wherein said cells are enriched for CD34+ cells.

5. The method of claim 1, wherein said stem cells or progenitor cells are derived from bone marrow, umbilical cord, peripheral blood, or mobilized peripheral blood.

6. The method of claim 1, wherein said stem cells and/or progenitor cells comprise embryonic stem cells, adult stem cells, or induced pluripotent stem cells.

7. The method of claim 1, wherein said notch ligand is provided by co-culture with stroma cells comprising stem cells.

8. The method of claim 7, wherein said stem cells are mesenchymal stem cells (MSCs).

9. The method of claim 7, wherein said stroma cells comprise induced pluripotent stem cells (IPSCs) or derivatives of IPSCs, or human embryonic stem cells.

10. The method of claim 1, wherein said culture comprises: minimum essential medium (MEM) with L-alanyl-L-glutamine dipeptide; fetal calf serum or human AB serum; recombinant SCF; recombinant FLT3L; and IL-3 or GM-CSF.

11. The method of claim 10, wherein said culture comprises:
   about 5% human AB serum;
   about 5 ng/ml SCF;
   about 5 ng/ml FLT3L; and
   about 5 ng/ml IL-3 or about 10 ng/ml GM-CSF.

* * * * *